United States Patent [19]

Tobe et al.

[11] 4,182,724
[45] Jan. 8, 1980

[54] COMPOSITIONS CONTAINING PLATINUM

[75] Inventors: Martin L. Tobe, Northwood; Abdul R. Khokhar, London; Peter D. M. Braddock, Wigan, all of England

[73] Assignee: Rustenburg Platinum Mines Limited, Johannesburg, South Africa

[21] Appl. No.: 934,990

[22] Filed: Aug. 18, 1978

Related U.S. Application Data

[63] Continuation of Ser. No. 784,797, Apr. 5, 1977, Pat. No. 4,119,653.

[30] Foreign Application Priority Data

Apr. 6, 1976 [GB] United Kingdom ............... 13888/76

[51] Int. Cl.$^2$ ............................................. C07F 15/00
[52] U.S. Cl. ................................. 260/429 R; 424/287
[58] Field of Search ..................................... 260/429 R

[56] References Cited

U.S. PATENT DOCUMENTS

| 4,119,653 | 10/1978 | Tobe et al. ................. | 260/429 R |
| 4,119,654 | 10/1978 | Tobe et al. ................. | 260/429 R |

OTHER PUBLICATIONS

Chemical Abstracts, 78, 115716r (1973).
JACS 95(6), pp. 2047-2048 (1973).
Braddock et al., Chem. Biol. Interact. 11(3), pp. 145-161 (1975).
Tobe et al., J. Clin. Hematol. Oncol. 7(1), pp. 114-137 (1977).

*Primary Examiner*—Helen M. S. Sneed
*Attorney, Agent, or Firm*—Cushman, Darby & Cushman

[57] ABSTRACT

This invention relates to a compound of platinum having the structure:

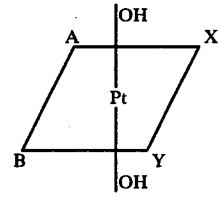

in which X and Y are halogenoid groups which are the same or different and are preferably both chloride but may be other halide or pseudohalide such as cyanate, thiocyanate and azide or other similar groups, and A and B are the same or different and are selected from the group consisting of ammonia, $NH_3$ and straight chain aliphatic amine groups co-ordinated to the Pt through their N atoms.

1 Claim, No Drawings

COMPOSITIONS CONTAINING PLATINUM

This is a continuation of application Ser. No. 784,797 filed Apr. 5, 1977, now U.S. Pat. No. 4,119,653.

This invention relates to new compositions of matter containing platinum.

According to one aspect of the present invention a composition of matter comprises a co-ordination compound of platinum having the structure:

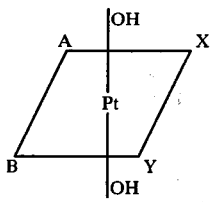

in which X and Y are halogenoid groups which are the same or different and are preferably both chloride but may be other halide or pseudohalide such as cyanate, thiocycnata and azide and A and B are the same or different and are selected from the group consisting of ammonia, $NH_3$, and straight chain aliphatic amine groups co-ordinated to the Pt through their N atoms.

According to a second aspect of the present invention there is applied a co-ordination compound of platinum having the structure:

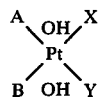

in which X and y are halogenoid groups which are the same or different and are preferably both chloride but may be other halide, pseudohalide such as cyanide, cyanate, thiocyanate, or axide or other similar groups and A and B are the same or different and are selected from the group consisting of ammonia and straight chain aliphatic amine groups or C-substituted branched chain aliphatic amine groups co-ordinated to the Pt through their N atoms each having the general formula:

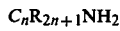

in which n may vary from 3 to 9 and in which all of the R groups are either the same or different and are preferably all hydrogen but may be selected from the group consisting of hydrogen, alkyl, aryl, alkaryl, aralkyl, halogen, pseudohalogen, hydroxy, carbonyl, formyl, nitro, amido, amino, sulphonic acid, sulphonic acid salt, carboxylic acid, carboxylic acid salt, and substituted alkyl, aryl, alkaryl and aralkyl groups.

The platinum is preferably present as $Pt^{4+}$, thus producing a neutral complex with two hydroxyl and two halide ligands.

Although R groups other than hydrogen are not normally preferred, they may be used and may comprise lower alkyl such as methyl or ethyl or a solubilizing group such as a sulphonic acid group. Solubilizing groups as substituents such as carboxylic acid, sulphonic acid, carboxylic acid salt, sulphonic acid salt, e.g., the sodium, potassium or lithium salts, are sometimes appropriate when the clinical conditions require high solubility.

Throughout the specification and claims, the term "halogenoid" is used to mean halide (chloride, bromide, iodide or fluoride) or pseudohalide such as cyanide, cyanate, thiocyanate or azide.

Suitable straight chain amine compounds which may be used for groups A and B are 1-aminohexane, 1-aminoheptane and 1-aminooctane.

Results obtained using trans di-hydroxo complexes of Pt(IV) where in the above formula X and Y are both chloride and A and B are the same molecule (ammonia) are as follows:

| Tumour: | ADJ/PC6 | | | |
|---|---|---|---|---|
| Vehicle: | Arachis oil/Intraperitoneal | | | |
| Subject: | Balb-c white mice | | | |
| mgm/Kgm | % Inhibition | $ED_{90}$ | $LD_{50}$ | TI |
| 12 | 95.4 | <12 | 135 | >11.2 |
| 60 | 97.1 | | | |
| 300 | 3D/3* | | | |
| 1500 | 3D/3* | | | |

*Three deaths in three animals.

The therapeutic index (TI) is, therefore, greater than 11.25.

METHODS OF PREPARATION

A preferred method of preparation of trans dihydroxo cis dichloro diamine (or diammine where $A=B=NH_3$) Pt(IV) complexes from the corresponding Pt(II) complex is as follows:

20 g. of cis-[$PtCl_2$(normal-$C_nH_{2n+1}NH_2)_2$]

is slurried in hot water (50 ml.) and 100 ml. (30%W/V) aqueous hydrogen peroxide is added. The suspension is boiled for 30 minutes, cooled to room temperature and chilled overnight before filtration. The crude product is washed with a minimum of water and ethanol and then air dried. The crude product (69% by weight yield) is recrystallised from $H_2O_2$ (15 ml. of 30% W/V) in 280 ml. water and dried in vacuo at 50° C. overnight. Yield: 35%.

Preparation of n-alkylamine platinum IV complexes

[$PtCl_4$ (n-$RNH_2)_2$] and [$PtCl_2(OH)_2$ (n-$RNH_2)_2$]

where R=
  $C_3H_7$—propyl
  $C_4H_9$—butyl
  $CH_3OC_3H_6$—3 methoxypropyl
  $C_8H_{17}$—octyl 1. Preparation of cis-$PtCl_2$(n-$C_3H_7NH_2)_2$—the starting material used for the preparation of the test compounds.

$K_2[PtCl_4]$(50 g) was dissolved in water (500 ml), stirred with charcoal and filtered on a porosity 4 filter. Potassium iodide (79 g) in water (200 ml) was added to the filtrate and stirred for 5 minutes before addition of n-propylamine (21.5 ml). The mixture was stirred at room temperature for 2 hours, filtered and the [$PtI_2$(n-$C_3H_7NH_2)_2$] washed with water, ethanol and dried in vacuo.

Yield 63.9 g, 94%.

This product was slurried in water (200 ml) at 40° C. and an aqueous solution of silver nitrate (38 g 100 ml)

was added and stirred for 2 hours. The precipitate of AgI was filtered off, washed with water and the filtrate tested for excess silver by addition of one crystal of NaCl. Concentrated hydrochloric acid (50 ml.) was added to the silver free solution and stirred at 40° C. for two hours. The slurry of crude product was cooled overnight, filtered and the residue washed with water ethanol and dried in vacuo. The crude product was recrystallised from NN dimethylformamide (500 ml) by addition of 1 liter of 0.1 N hydrochloric acid.

Yield: 36.7 g, 80%

IR$\nu$Pt-Cl 320 cm$^{-1}$

Preparation of cis - PtCl4(n-C$_3$H$_7$NH$_2$)$_2$ cis - PtCl$_2$(n-C$_3$H$_7$NH$_2$)$_2$ (10 g) was slurried in water (70 ml.) and heated to 70° C. Chlorine was bubbled through the suspension for 1 hour during which time the slurry changed colour from pale to dark yellow. The chlorine flow was stopped and the slurry boiled for 5 minutes to remove excess chlorine before chilling at 0° C. overnight. The product was filtered off, washed with water, ethanol and dried in vacuo.

Yield 9.9 g, 83.5%

IR$\nu$Pt-Cl 340 cm$^{-1}$.

Preparation of PtCl$_2$(OH)$_2$(n-C$_3$H$_7$NH$_2$)$_2$ cis- PtCl$_2$(n-C$_3$H$_7$NH$_2$)$_2$ (13 g) was slurried in water (25 ml.) and boiled for 0.5 hours with hydrogen peroxide solution (37%, 50 ml.). The slurry changed colour from pale to dark yellow and was chilled overnight at 0° C. before filtering off the product which was washed with water, ethanol and dried in vacuo.

Yield: 11.6 g, 79%

IR$\nu$Pt-Cl 333 cm$^{-1}$.

Reaction pathway:

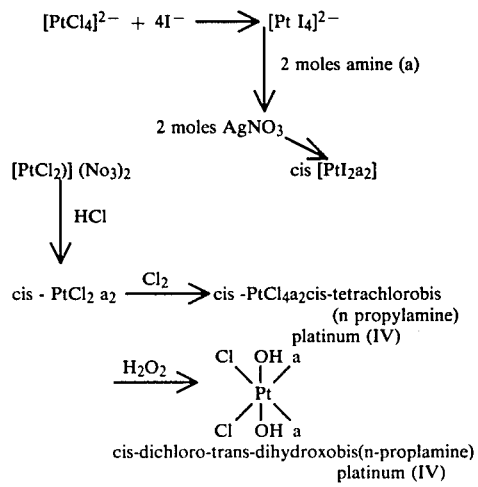

cis-dichloro-trans-dihydroxobis(n-proplamine) platinum (IV)

| Elemental assays. | Pt | C | H | N | O | Cl |
|---|---|---|---|---|---|---|
| PtCl$_2$(n-C$_3$H$_7$NH$_2$)$_2$ | 50.79 | 18.75 | 4.69 | 7.29 | — | 18.48 |
| found | — | 18.85 | 4.74 | 7.32 | — | 18.42 |
| PtCl$_4$(n-C$_3$H$_7$NH$_2$)$_2$ | 42.87 | 15.82 | 3.96 | 6.15 | — | 31.20 |
| found | — | 15.90 | 4.04 | 6.07 | — | 30.77 |
| PtCl$_2$(OH)$_2$(n-C$_3$H$_7$NH$_2$)$_2$ | 46.66 | 17.22 | 4.78 | 6.70 | 7.65 | 16.98 |
| found | — | 7.23 | 4.82 | 6.60 | 7.69 | 16.75 | f

The same methods were used for the n-butyl and 3-methoxypropyl complexes i.e. cis-[PtCl$_2$(n-C$_4$H$_9$NH$_2$)$_2$]
| crude yield | [PtI$_2$(n-C$_4$H$_9$NH$_2$)$_2$] | = | 98% |
| crude yield | [PtCl$_2$(n-C$_4$H$_9$NH$_2$)$_2$] | = | 85% |
| pure | [PtCl$_2$(n-C$_4$H$_9$NH$_2$)$_2$] | = | 62% |
| " | [PtCl$_4$(n-C$_4$H$_9$NH$_2$)$_2$] | = | 85% |
| " | [PtCl$_2$(OH)$_2$(n-C$_4$H$_9$NH$_2$)$_2$] | = | 80% |

| Elemental analysis | Pt | C | H | N | O | Cl |
|---|---|---|---|---|---|---|
| [PtCl$_2$(n-C$_4$H$_9$NH$_2$)$_2$] | 47.34 | 23.30 | 5.34 | 6.79 | — | 17.23 |
| [PtCl$_4$(n-C$_4$H$_9$NH$_2$)$_2$] | 40.39 | 19.87 | 4.55 | 5.80 | — | 29.39 |
| [PtCl$_2$(OH)$_2$(n-C$_4$H$_7$NH$_2$)$_2$] | 43.73 | 21.52 | 5.38 | 6.28 | 7.17 | 15.92 |
| | — | 21.78 | 5.45 | 6.34 | 7.25 | 15.63 |

Infra-red spectrum (IR)

The IR values for the following complexes are as indicated below:

IR [PtCl$_2$(n-butylNH$_2$)$_2$]$\nu$Pt-Cl: 322 cm$^{-1}$;
[PtCl$_4$(n-butylNH$_2$)$_2$]$\nu$Pt-Cl: 330,340,350 cm$^{-1}$;
[PtCl$_2$(OH)$_2$(n-butylNH$_2$)$_2$]$\nu$Pt-Cl: 335 cm$^{-1}$.

| a = CH$_3$OC$_3$H$_6$NH$_2$ complexes | Yield |
|---|---|
| crude PtI$_2$a$_2$ | 90% |
| pure PtCl$_2$a$_2$ | 71% |
| IR $\nu$PtCl = 318 cm$^{-1}$ | |
| PtCl$_4$a$_2$ = | 27% |
| IR $\nu$PtCl = 330,349 cm$^{-1}$ | |
| PtCl$_2$(OH)$_2$a$_2$ | 30% |
| IR $\nu$PtCl = 340 cm$^{-1}$ | |

The IR results indicate the oxidation state of the platinum. All the complexes tested are of Pt(IV), for which the typical Pt-Cl stretching frequency is in the region of 330-350 cm$^{-1}$. The starting material, on the other hand, (i.e. cis-PtCl$_2$(n-C$_n$H$_{2n+1}$NH$_2$)$_2$, being Pt(II), has a typical Pt-Cl stretching frequency of about 220 cm$^{-1}$.

| Elemental analysis% | Pt | C | H | N | O | Cl |
|---|---|---|---|---|---|---|
| PtCl$_2$a$_2$(calculated) | 43.93 | 21.62 | 4.95 | 6.30 | 7.20 | 15.79 |
| (found) | | 21.69 | 4.96 | 6.37 | 7.48 | 15.75 |
| PtCl$_4$a$_2$(calculated) | 37.88 | 18.64 | 4.27 | 5.44 | 6.21 | 27.57 |
| (found) | | 19.10 | 4.40 | 5.52 | 6.24 | 25.87 |
| PtCl$_2$(OH)$_2$a$_2$(calculated) | 40.81 | 20.08 | 5.02 | 5.86 | 13.39 | 14.85 |
| (found) | | 20.01 | 5.03 | 5.90 | 13.42 | 14.62 |

The n-octylamine PtII complex was prepared by a different method, namely,

K$_2$[PtCl$_4$] (25 g) was dissolved in water (250 ml) and filtered through charcoal on a porosity 4 filter n-octylamine (22.5 ml) was added to the filtrate and stirred for two hours to give a white precipitate which was filtered off, washed with water, ethanol, ether and dried in vacuo. The crude product was recrystallised from DMF/O.IN CCl as before.

Yield 80%

PtCl$_4$$^{2-}$ + 2 amine → cis - PtCl$_2$(a)$_2$ $\nu$Pt-Cl = 322 cm$^{-1}$

The PtCl$_4$a$_2$ derivative was prepared as before

Yield 76%

$\nu$Pt-Cl=320 sh., 345 cm$^{-1}$

| Elemental analysis | Pt | C | H | N | Cl |
|---|---|---|---|---|---|
| PtCl$_4$a$_2$ | 32.78 | 32.26 | 6.39 | 4.71 | 23.86 |
| | | 32.27 | 6.45 | 4.79 | 24.01 |

The following table is a summary of the results obtained using the trans-dihydroxy complexes specified and indicate a therapeutic index (TI) greater than 11.2. Again as with the results given earlier, the tumour was ADJ/PC6, the vehicle was Arachis oil administered intraperitoneally to Balb-c white mice.

| Complex | LD$_{50}$ mg/kg | ID$_{90}$ mg/kg | TI |
|---|---|---|---|
| trans-OH n-pentyl | 665 | 37.5 | 17.7 |
| Cl$_4$ n-pentyl | 26.5 | <12 | >2.2 |
| trans-OH n-butyl | 220 | 12.5 | 17.6 |
| Cl$_4$ n-butyl | 56 | <5 | >11.2 |
| Cl$_4$ n-octyl | 270 | — | — |
| | (<20% inhib) | | |

What is claimed is:

1. An alkylamine platinum IV complex having the structure:

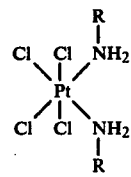

wherein R is butyl, pentyl, octyl or 3-methoxypropyl.

* * * * *